US012214107B2

(12) United States Patent
Luo et al.

(10) Patent No.: US 12,214,107 B2
(45) Date of Patent: Feb. 4, 2025

(54) DRUG-COATED MEDICAL DEVICES

(71) Applicants: Vascuros Medical (Shanghai) Co., Ltd., Shanghai (CN); Vascuros Medical Pte Ltd., Jtc Medtech Hub (SG)

(72) Inventors: Jingnan Luo, Medtech Hub (SG); Qian Yi Michele Lee, Medtech Hub (SG); Honglei Wang, Medtech Hub (SG)

(73) Assignees: Vascuros Medical (Shanghai) Co., Ltd. (CN); Vascuros Medical Pte Ltd., Singapore (SG)

( * ) Notice: Subject to any disclaimer, the term of this patent is extended or adjusted under 35 U.S.C. 154(b) by 0 days.

(21) Appl. No.: 17/849,426

(22) Filed: Jun. 24, 2022

(65) Prior Publication Data
US 2023/0057153 A1 Feb. 23, 2023

Related U.S. Application Data

(63) Continuation of application No. 15/742,828, filed as application No. PCT/SG2016/050318 on Jul. 8, 2016, now abandoned.

(30) Foreign Application Priority Data

Jul. 9, 2015 (GB) .................................. 1512030

(51) Int. Cl.
| | | |
|---|---|---|
| A61F 2/00 | (2006.01) | |
| A61K 31/337 | (2006.01) | |
| A61K 31/436 | (2006.01) | |
| A61L 29/08 | (2006.01) | |
| A61L 29/16 | (2006.01) | |
| A61M 25/10 | (2013.01) | |

(52) U.S. Cl.
CPC ............ *A61L 29/16* (2013.01); *A61K 31/337* (2013.01); *A61K 31/436* (2013.01); *A61L 29/085* (2013.01); *A61M 25/1029* (2013.01); *A61L 2300/416* (2013.01); *A61L 2300/62* (2013.01); *A61L 2300/622* (2013.01); *A61L 2300/624* (2013.01); *A61L 2420/02* (2013.01); *A61M 2025/1004* (2013.01); *A61M 2025/1031* (2013.01); *A61M 2025/105* (2013.01); *A61M 2025/1075* (2013.01)

(58) Field of Classification Search
CPC ........ A61F 2/00; A61F 2/0013; A61F 2/0027; A61F 2/0036; A61F 2/004; A61F 2002/01; A61F 2002/016; A61F 2002/018
See application file for complete search history.

(56) References Cited

U.S. PATENT DOCUMENTS

| 8,257,308 | B2 | 9/2012 | Bianchi et al. | |
|---|---|---|---|---|
| 2005/0004663 | A1* | 1/2005 | Llanos ................. | A61B 17/11 623/1.46 |
| 2005/0232969 | A1 | 10/2005 | Andre et al. | |
| 2008/0255510 | A1 | 10/2008 | Wang | |
| 2010/0272774 | A1 | 10/2010 | Chappa et al. | |
| 2011/0159169 | A1 | 6/2011 | Wang | |
| 2011/0160645 | A1 | 6/2011 | Sutermeister | |
| 2011/0190864 | A1* | 8/2011 | McClain ................. | A61F 2/958 623/1.46 |
| 2011/0295200 | A1 | 12/2011 | Speck et al. | |
| 2013/0190689 | A1 | 7/2013 | Slager | |
| 2013/0197434 | A1 | 8/2013 | Wang | |
| 2013/0302381 | A1 | 11/2013 | Barnett et al. | |
| 2014/0228752 | A1 | 8/2014 | Speck et al. | |
| 2014/0336571 | A1 | 11/2014 | Slager et al. | |

FOREIGN PATENT DOCUMENTS

| WO | 2001078626 A1 | 10/2001 | |
|---|---|---|---|
| WO | 2011109508 A2 | 9/2011 | |
| WO | 2012039884 A1 | 3/2012 | |
| WO | WO-2012166819 A1 * | 12/2012 | ........... A61L 29/085 |
| WO | 2013007273 A1 | 1/2013 | |
| WO | 2014029442 A1 | 2/2014 | |

(Continued)

OTHER PUBLICATIONS

International Search Report and Written Opinion dated Aug. 17, 2016 for Application No. PCT/SG2016/050318.
A. Seidlitz, et al., In Vitro Determination of Drug Transfer from Drug-Coated Balloons, PLoS One, 2013, 8 e83992.
J. F. Granada, et al., Mechanisms of tissue uptake and retention of paclitaxel-coated balloons: impact on neointimal proliferation and healing, Open Heart, 2017, 1, e000117.
UK Search Report dated Dec. 21, 2015 for Application No. GB1512030.6.
EP extended search report for related Application No. 16821752.9 dated Feb. 5, 2019.

(Continued)

*Primary Examiner* — Micah Paul Young
(74) *Attorney, Agent, or Firm* — Patterson + Sheridan, LLP

(57) ABSTRACT

Disclosed herein is a drug-coated medical device in the form of a balloon having an inner surface and an outer hydrophobic surface, an adhesion balance layer directly on the outer hydrophobic surface of the balloon, comprising a hydrophilic polymer and/or a hydrophilic compound where the hydrophilic compound has a molecular weight of less than 1,000 Daltons, and a therapeutic layer directly on the adhesion balance layer comprising a therapeutic agent and a pharmaceutically acceptable carrier, wherein the therapeutic agent is a hydrophobic therapeutic agent with one or more hydrogen-bonding groups and is provided as discrete drug particles in the therapeutic layer, the drug particles have at least one dimension that is less than 25 μm and are uniformly distributed on the surface of the balloon, and the pharmaceutically acceptable carrier is hydrophilic and has a molecular weight of less than 1,000 Daltons. A process to make the drug-coated medical device and uses thereof are also disclosed.

18 Claims, 8 Drawing Sheets

(56) References Cited

FOREIGN PATENT DOCUMENTS

| WO | 2014163097 A1 | 10/2014 |
| WO | 2014186729 A1 | 11/2014 |

OTHER PUBLICATIONS

EP examination report for related Application No. 16821752.9 dated Jan. 17, 2020.
EP Office Action for related Application No. 16821752.9 dated Oct. 7, 2020.
Carlyle et al., Enhanced drug delivery capabilities from stents coated with absorbable polymer and crystalline drugs; Journal of Controlled Release, 162, 2012, 561-567 (Year: 2012).

* cited by examiner

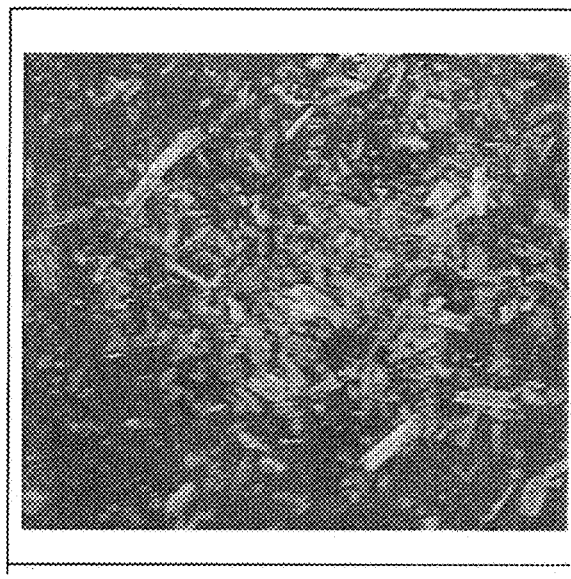 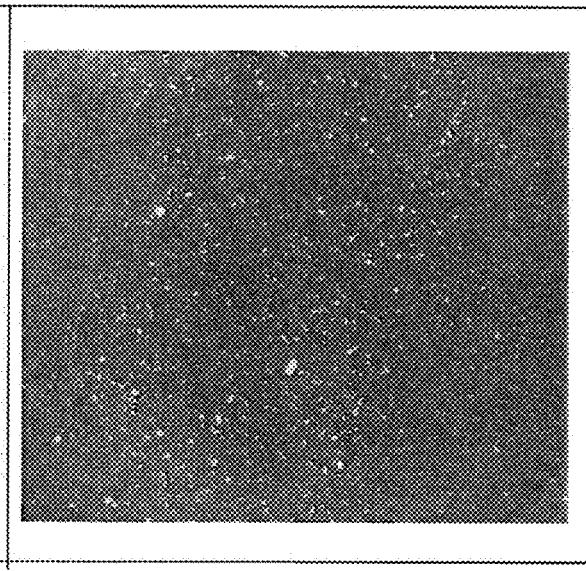
FIG. 11A    FIG. 11B
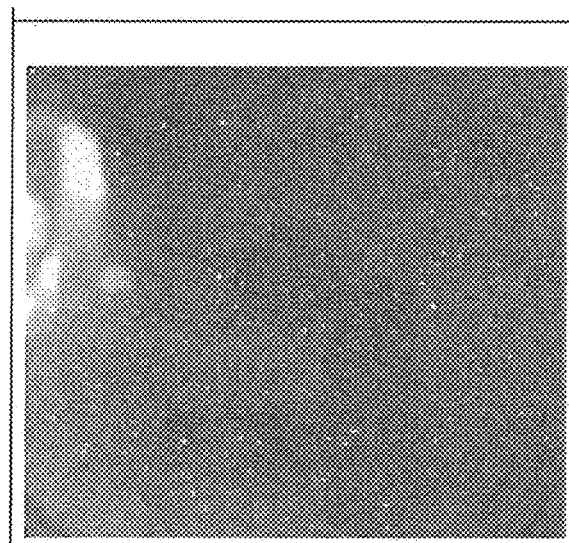 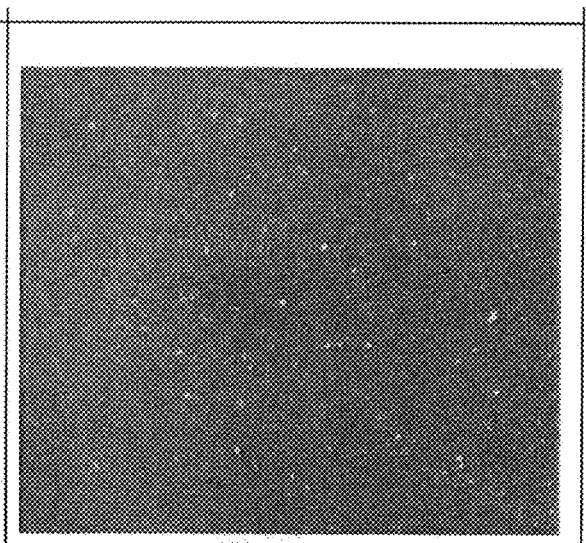
FIG. 11C    FIG. 11D

DRUG-COATED MEDICAL DEVICES

CROSS-REFERENCE TO RELATED APPLICATIONS

This application is a continuation of co-pending U.S. patent application Ser. No. 15/742,828, filed Jan. 8, 2018, which is a 371 of International Application No. PCT/SG2016/050318, filed Jul. 8, 2016, which claims priority to United Kingdom Patent Application No. 1512030.6 filed Jul. 9, 2016. Each of the aforementioned related patent applications is herein incorporated by reference.

BACKGROUND

Field

This invention relates to the field of drug-coated medical devices, particularly catheter balloons, and methods for their preparation and use in medical treatment.

Description of the Related Art

Coronary/Peripheral Artery Disease is a common circulatory problem in which plaque builds up in the arteries and limits blood flow to parts of the body. A typical treatment for this condition includes artery bypass surgery, stent placement or balloon angioplasty.

In the case of stent placement and balloon angioplasty, some patients develop a new narrowing of the vessel wall, termed as stenosis, at the site of intervention after a few months. Should stenosis reoccur, either due to the original stent placement and balloon angioplasty, or due to the removal of the original stent or fitting of a new stent, then the resulting narrowing of the vessel wall is known as restenosis. The recognition of the problems associated with stenosis and restenosis resulted in the development of drug eluting stents. A drug eluting stent is designed to release one or more drugs for a sufficiently long time span to inhibit cell hyper-proliferation (and hence stenosis/restenosis). However, the use of drug eluting stents poses a risk of inflammation due to chronic irritation from a permanent implant. Thus, a device capable of a fast release of a therapeutic dose to the treatment site would be preferred over a permanent implant.

Typically, a drug eluting stent comprises a repeating unit cell of struts that can be compressed for delivery and expanded upon reaching the desired site of activity within the artery lumen and a coating layer on the struts that contains the one or more drugs for elution. This typical design results in another important limitation to the use of drug eluting stents, which is the non-uniform distribution of drugs in the polymer matrix of the coating. The drug is effectively concentrated on the struts of the stent, resulting in non-uniform drug release to the tissue of the vessel wall, which may cause tissue damage and thrombosis in areas exposed to excess drug and hyperplasia and stenosis or restenosis (when the subject has already suffered stenosis) in areas that are undertreated. Hence, there is a need for a device capable of a uniform drug transfer to the target tissue.

More recently, the concept of a drug eluting balloon (DEB) has been introduced in which angioplasty balloons are coated with an active agent. In practice, the DEB transfers the active agent to the vessel wall when the balloon is inflated and pressed against the vessel wall.

While some DEBs were proven to be effective in practice, this class of device presents new challenges and problems. These problems and challenges can be summarised as follows.

It is important that the drug is sufficiently retained on the balloon surface during the handling and delivery process so as to reduce the loss of the active agent before the balloon reaches the target site.

It is important that the therapeutic drug dose is rapidly released to the target vessel during the very short contact time of the angioplasty procedure. Ideally, the drug is absorbed into the vessel wall before it can be diluted/washed off by the flow of blood through the vessel, and that a therapeutic dose is sustained at the target site for a period of time (i.e. the period required to ensure that stenosis/restenosis is reduced or suppressed).

It is also important that the coated drug particles are released in a well-controlled manner. If many large particles or particle aggregates produced following balloon inflation there is always a concern that the coating particulate will cause microvessel embolization.

The drug coating must also be stable, such that it does not crack upon the expansion and contraction of the device, and does not peel off during delivery. The cracking or peeling of the drug coating may release active particles (e.g. particles of the active ingredient) into the bloodstream, which can lead to undesirable and potentially severe reactions due to systemic toxicity or distal embolization.

Previously described drug-coated balloons have looked into various ways to improve the drug transfer efficiency of the coating or to reduce drug loss. Most previously described balloons consist of a single therapeutic layer, with the use of small and hydrophilic molecules as carriers (such as urea, sorbitol, polysorbate, micelles, oil or lipid excipients, contrast agents, iopromide, loversol, reseveratol, surfactants, Tween 20, Tween 40, Tween 80 and sodium alginate polysaccharide). More often than not, an improvement of drug transfer efficiency leads to an increase in drug loss and vice versa, a balance between the two has not been achieved using this approach.

In international application publication number WO 2013/007273, the use of a base coat of shellac is described. This coating comprises a first base coat of shellac, a second layer of an active agent with a concentration gradient and a top layer of shellac. The base coat technology described therein functions more as a carrier to improve drug transfer to the target vessel. Therefore, the technology described by WO 2013/007273 is restricted to the current design and may not be effective if the therapeutic layer requires a carrier. In addition, problems encountered with this design may include the dislodgement of large drug patches or large drug particle aggregates following deployment due to the presence of the polymer in both the base layer and in the drug layer.

Other problems faced by prior art drug-coated balloons include inconsistent drug particle distribution and inconsistent therapeutic outcomes. The ideal DEB can be defined as achieving a uniform coating that minimizes the quantity of particles released and provides maximal drug retention with minimal vascular toxicity. Therefore, the drug-coated balloons described previously have been unable to strike a balance between a uniform coating with high drug transfer and low drug loss, such as by loss of patches, large aggregates particles and the like into the blood stream of a subject.

Hence, there remains a need to develop a stable and uniform coating for balloons that can rapidly release therapeutic agents in an effective and efficient manner in the form of individual particles rather than particle aggregates or large patches following deployment, with little loss of the drug en route to the desired site of action.

SUMMARY

The current invention surprisingly provides a more uniform coating on the surface of the balloon, which translates into a uniform coating of small, discrete drug particles following deployment that are less susceptible to loss of the drug particles in patches and/or as large aggregates in the body lumen.

In a first aspect of the invention, there is provided a drug-coated medical device comprising:

a balloon having an inner surface and an outer hydrophobic surface;

an adhesion balance layer directly on the outer hydrophobic surface of the balloon, comprising a hydrophilic polymer and/or a hydrophilic compound where the hydrophilic compound has a molecular weight of less than 1,000 Daltons; and a therapeutic layer directly on the adhesion balance layer comprising a therapeutic agent and a pharmaceutically acceptable carrier, wherein:

the therapeutic agent is a hydrophobic therapeutic agent with one or more hydrogen-bonding groups and is provided as discrete drug particles in the therapeutic layer;

the drug particles have at least one dimension that is less than 25 μm and are uniformly distributed on the surface of the balloon; and the pharmaceutically acceptable carrier is hydrophilic and has a molecular weight of less than 1,000 Daltons.

In embodiments of the invention, the medical device may be a catheter balloon for a balloon catheter or may be a balloon catheter.

In yet further embodiments of the invention:

(i) the thickness of adhesion balance layer may be from 0.01 to 30 μm, such as from 0.01 to 10 μm (e.g. from 0.01 to 4 μm, such as from 0.1 to 2 μm) when measured in a dry state;

(ii) the hydrophilic polymer and/or a hydrophilic compound in the adhesion balance layer contains hydrogen bonding moieties;

(iii) the drug particles may have at least one dimension that is less than 15 μm (e.g. less than 10 μm);

(iv) the amount of carrier to therapeutic agent in the therapeutic layer may be from 1:8 to 8:1 wt/wt (e.g. from 1:4 to 3:1 wt/wt);

(v) the adhesion balance layer may swell or absorb water when in contact with water;

(vi) the hydrophilic polymer may be selected from one or more of the group consisting of poly (lactams), polyurethanes, homo- and copolymers of acrylic and methacrylic acid, polyvinyl alcohol, polyvinylethers, polyethers, maleic anhydride-based copolymers, vinylamines, polyethyleneimines, poly (carboxylic acids), polyamides, polyanhydrides, polyphosphazenes, cellulosics, heparin, dextran, polypeptides, polysaccharides, polyesters, oligopeptides, oligonucleotides, and copolymers and derivatives thereof (e.g. a polyether, a derivative or a copolymer thereof, such as a polyether selected from one or more of the group consisting of polyoxymethylene (POM), polyethylene glycol (PEG), polypropylene glycol (PPG), polytetrahydrofuran (PTHF), derivatives thereof and copolymers thereof (e.g. polyether may be selected from one or more of polyethylene glycol, polyethylene glycol derivatives, and copolymers thereof));

(vii) the adhesion balance layer may further comprise a hydrophobic polymer (e.g. the polymer layer may contain less than 30 wt % of the hydrophobic polymer and/or wherein the hydrophilic polymer and/or hydrophobic polymer may not be shellac);

(viii) the hydrophilic polymer may be a block copolymer comprising hydrophobic and hydrophilic blocks, optionally wherein the hydrophobic polymer and the hydrophobic polymer blocks may be less than 30 wt % of the hydrophilic polymer;

(ix) the hydrophilic polymer may have a number average molecular weight of from 10,000 to 10,000,000 Daltons, such as from 100,000 to 5,000,000 Daltons, for example, from 500,000 to 2,000,000 Daltons;

(x) the therapeutic agent of the therapeutic agent layer may be selected from one or more of the group consisting of an antiproliferative, immunosuppressive, anti-angiogenic, anti-inflammatory, and anti-thrombotic agent (e.g. the therapeutic agent may be selected from one or more of the group consisting of paclitaxel, rapamycin, everolimus, zotarolimus, umirolimus, tacrolimus, and pimecrolimus (such as a therapeutic agent selected from one or more of the group consisting of paclitaxel, rapamycin, zotarolimus and umirolimus, such as paclitaxel and rapamycin));

(xi) the adhesion balance layer may further comprise a therapeutic agent, optionally wherein the therapeutic agent in the adhesion balance layer may be as defined hereinbefore;

(xii) the hydrophilic compound with a molecular weight of less than 1,000 Daltons may be selected from one or more of the group consisting of a sugar, a sugar alcohol, and polyethylene glycol (e.g. the hydrophilic compound with a molecular weight of less than 1,000 Daltons may be selected from one or more of the group consisting of fructose, glucose, sucrose, lactose, maltose, erythritol, threitol, arabitol, ribitol, mannitol, galactitol, fucitol, iditol, inositol, volemitol, isomalt, maltitol, lactitol, maltotriitol, maltotetraitol, xylitol, sorbitol and polyethylene glycol (such as selected from one or more of the group consisting of fructose, glucose, sucrose, xylitol, mannitol, and sorbitol));

(xiii) the pharmaceutically acceptable carrier may be selected from one or more of the group consisting of tartaric acid, a sugar, and a sugar alcohol (e.g. the pharmaceutically acceptable carrier may be selected from one or more of the group consisting of fructose, glucose, sucrose, lactose, maltose, erythritol, threitol, arabitol, ribitol, mannitol, galactitol, fucitol, iditol, inositol, volemitol, isomalt, maltitol, lactitol, maltotriitol, maltotetraitol, more particularly, xylitol, tartaric acid, and sorbitol (such as selected from one or more of the group consisting of fructose, glucose, sucrose, mannitol, or more particularly, sorbitol, or yet more particularly xylitol, and tartaric acid));

(xiv) the therapeutic agent may be present in a total loading on the balloon of from 1 $\mu g/mm^2$ to 10 $\mu g/mm^2$ (e.g. from 1.5 $\mu g/mm^2$ to 4 $\mu g/mm^2$, such as from 2 $\mu g/mm^2$ to 3 $\mu g/mm^2$);

(xv) the therapeutic and adhesion balance layers may provide a uniform coating over the outer surface of the balloon, optionally wherein the uniform surface may be interrupted by lines caused by folds in the balloon;

(xvi) the balloon may form an integral or removable part of a balloon catheter;

(xvii) the drug particles may be provided in the form of one or more of the group selected from particulate needles, microparticles and nanoparticles.

It will be appreciated that the above embodiments of the invention may be combined in any technically sensible manner by a person skilled in the art. All such technically sensible combinations are explicitly contemplated as forming part of the current invention.

In a second aspect of the invention, there is provided a process to make a drug-coated medical device, wherein the process comprises:

(a) providing an uncoated balloon;

(b) providing an adhesion balance layer precursor mixture, coating at least part of the outer surface of balloon with the adhesion balance layer precursor mixture to form an adhesion balance layer precursor layer and drying the adhesion balance layer precursor layer to provide a balloon coated with an adhesion balance layer;

(c) providing a therapeutic agent mixture and coating the therapeutic agent solution onto the outer surface of the balloon coated with an adhesion balance layer, followed by drying the coated balloon to provide the drug-coated catheter balloon, wherein therapeutic agent mixture comprises a hydrophobic therapeutic agent with one or more hydrogen-bonding groups, a solvent and a hydrophilic pharmaceutically acceptable carrier that has a molecular weight of less than 1,000 Daltons; and the adhesion balance layer precursor mixture comprises a hydrophilic polymer and/or a hydrophilic compound, where the hydrophilic compound has a molecular weight of less than 1,000 Daltons.

It will be appreciated that the balloon used herein may be provided in a folded state and so may be coated in this folded state. Alternatively, the process may further comprise the steps of:

(i) inflating the balloon between step (a) and (b), optionally wherein the inflation is to a pressure of 2 atm ($2.0265 \times 10^5$ P);

(ii) deflating the balloon following step (c); and (iii) folding the balloon following step (ii).

In embodiments of the invention, the adhesion balance layer precursor mixture may comprise the hydrophilic polymer and/or the hydrophilic compound in combination with a solvent selected from one or more of the group consisting of water, acetone, acetonitrile or a $C_{1-4}$ alcohol (e.g. ethanol). The hydrophilic polymer may be present at a concentration of from 0.167 mg/mL to 20 mg/ml (e.g. from 0.2 mg/mL to 20 mg/mL) in the adhesion balance layer precursor mixture. In certain embodiments, the adhesion balance layer precursor mixture may further comprise a hydrophobic polymer.

In yet further embodiments of the invention, the therapeutic agent mixture may comprise a therapeutic agent and a solvent selected from one or more of the group consisting of dichloromethane, or more particularly, water, acetone, acetonitrile, tetrahydrofuran (THF) or a $C_{1-4}$ alcohol (e.g. ethanol or methanol), optionally wherein the therapeutic agent is present at a concentration of from 5 mg/mL to 100 mg/mL in the therapeutic agent mixture. The therapeutic agent of the therapeutic agent layer may be selected from one or more of the group consisting of an antiproliferative, immunosuppressive, anti-angiogenic, anti-inflammatory, and anti-thrombotic agent (e.g. the therapeutic agent may be selected from one or more of the group consisting of paclitaxel, rapamycin, everolimus, zotarolimus, umirolimus, tacrolimus, and pimecrolimus (such as a therapeutic agent selected from one or more of the group consisting of paclitaxel, rapamycin, zotarolimus and umirolimus, such as paclitaxel and rapamycin)).

In yet further embodiments of the invention:

(a) the carrier may be present at a concentration of from 0.5 mg/mL to 100 mg/ml (e.g. from 10 mg/mL to 50 mg/mL, such as from 20 mg/mL to 25 mg/mL) in the therapeutic agent mixture; and/or (b) the therapeutic agent may be present at a concentration of from 0.5 mg/mL to 100 mg/ml (e.g. from 20 mg/mL to 80 mg/mL, such as from 35 mg/mL to 65 mg/mL) in the therapeutic agent mixture.

In yet still further embodiments of the invention, the coating of steps (b) and (c) may be accomplished by one or more of the group consisting of brush coating, spraying, dipping, syringe depositing or pipette depositing, optionally wherein:

(i) the coating of step (b) is accomplished by dip coating; and/or (ii) the coating of step (c) is accomplished by spray coating.

In yet still further embodiments of the invention, drying the coated balloon in step (c) of the second aspect of the invention may use a temperature of from 35° C. to 100° C., such as from 40° C. to 60° C. (e.g. 45° C.).

In still further embodiments of the invention:

(a) the medical device may be a balloon catheter and the balloon is integrally formed as part of the balloon catheter; or (b) the process may further comprise fixing the balloon onto a balloon catheter either as a removable or integral part of said balloon catheter to form the medical device.

In a third aspect of the invention, there is provided the use of a drug-coated medical device according to the first aspect of the invention and any technically sensible combinations of its embodiments for use in medicine.

In a fourth aspect of the invention, there is provided a method of treatment using a drug-coated medical device as described in the first aspect of the invention and any technically sensible combinations of its embodiments to deliver a drug to a tissue in need of said treatment. For example, the method may further comprise the steps of:

(a) inserting the drug-coated medical device into a hollow tissue of a subject;

(b) advancing the medical device to a target site in a tissue;

(c) inflating the balloon and maintaining the inflated state for a period of time sufficient for the therapeutic agent to adhere to the target site;

(d) deflating the balloon and removing the medical device from the subject.

In certain embodiments, the period of time may be from 1 second to 2 minutes, such as from 30 seconds to 1 minute.

In embodiments of the invention, the method may be directed at treating and/or preventing stenosis or restenosis.

In a fifth aspect of the invention, there is provided a use of a drug-coated medical device as described in the first aspect of the invention and any technically sensible combinations of its embodiments for use in the delivery of a drug to a tissue in need of said treatment. For example, the treatment may be the treatment or prevention of stenosis or restenosis.

In a sixth aspect of the invention, there is provided a use of a drug-coated medical device as described in the first aspect of the invention and any technically sensible combinations of its embodiments in the preparation of a medicament for use in the delivery of a drug to a tissue in need of said treatment. For example, the treatment may be the treatment or prevention of stenosis or restenosis.

BRIEF DESCRIPTION OF THE DRAWINGS

Embodiments of the invention will now be described, by way of non-limiting example only, with reference to the accompanying drawings.

FIG. 5A compares drug coated balloon 1 (DCB1) with DCB 3; FIG. 5B compares DCB 2 with DCB 4; and FIG. 5C compares DCB 2 with DCB 5.

FIG. 6A compares DCB1 with DCB 3; FIG. 6B compares DCB 2 with DCB 4; and FIG. 6C compares DCB 2 with DCB 5.

FIGS. 9A and 9B relate to the SEM image of drug eluting balloon 8 (DEB8); FIGS. 9C and 9D relate to DEB9. FIGS. 9B and 9D are further magnifications of the images shown in FIGS. 9A and 9C, respectively.

FIGS. 10A and 10B relate to the SEM image of drug eluting balloon 10 (DEB10); FIGS. 10C and 10D relate to DEB11. FIGS. 10B and 10D are further magnifications of the images shown in FIGS. 10A and 10C, respectively.

FIGS. 11A-11D provide images of drug loss particle size in balloons of the current invention. FIG. 11A relates to the SEM image of drug eluting balloon 8 (DEB8); FIG. 11B relates to DEB9; FIG. 11C relates to DEB10; and FIG. 11D relates to DEB11.

DETAILED DESCRIPTION

Figure 1:
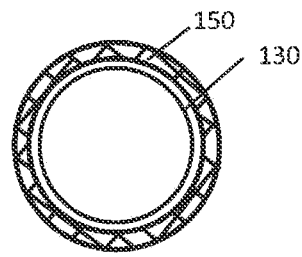
FIG. 1 depicts a cross-section of a prior art/comparative example drug coating on a balloon catheter, the coating having a single film layer that includes a therapeutic agent and a carrier.

The present invention relates to a drug-coated (or drug-eluting) balloon catheter consisting of an adhesion balance layer and a hydrophobic therapeutic layer. The adhesion balance layer is necessary to achieve a controllable adherence of a hydrophobic therapeutic layer on the hydrophobic surface of the balloon during the handling and delivery processes. It is usually the case that a coating solution used to form the therapeutic layer has a different surface energy compared to that of balloon surface. Given this, if the therapeutic layer is used alone it tends to form a non-uniform layer with either strong coherence or very weak coherence to the surface of the balloon, making the the therapeutic coating either very difficult or very easy, respectively, to remove from the surface of the balloon. Even when a carrier is used as part of the therapeutic layer, it is not easy to obtain a degree of control of the removal of the drug, leading to inconsistent drug release performance.

Surprisingly, it has been found that this problem of poor release performance can be solved by the introduction of a separate layer onto the surface of the balloon, such that it is between the hydrophobic balloon surface and the therapeutic layer. This separate layer may contain either a hydrophilic polymeric material or a hydrophilic compound (e.g. less than 1000 Daltons) and is described herein as the "adhesion balance layer". It is believed that the adhesion balance layer serves to balance the hydrophobic interaction between the therapeutic layer and the balloon surface (when the therapeutic layer further contains a hydrophilic carrier material). As such, it forms a stable coating layer in the dry state and it absorbs water, in a controllable manner, to achieve loose adherence with the therapeutic layer when the balloon is deployed in a subject. In other words, the adhesion balance layer increases the surface energy of the balloon surface and therefore improves the wetting of the therapeutic layer on the balloon, which in turn provides a more uniform therapeutic coating layer. Through controlling the chemistry of the adhesion balance layer, the adherence of the therapeutic layer can be well-tuned. That is, the adherence of the therapeutic layer can be adapted to suit the needs of the particular drug that is to be used. As a result, drug loss, drug release and drug tissue uptake can be tuned and well balanced, such that more of the drug is released at the desired site of action and without causing potentially harmful side effects.

The therapeutic layer comprises both a hydrophobic drug mixed with a hydrophilic carrier which has one or more hydrogen bonding groups in a single molecule. The function of this hydrophilic carrier material is to prevent strong adhesion between the drug particles and so may help to prevent release of large particle aggregates or large patches of the drug, either when en route to the desired site of action, or following deployment of the drug to the site of action. In addition, the use of the carrier, in combination with the adhesion balance layer may help to ensure efficient drug delivery. In addition, it has been surprisingly found that it is possible to control the morphology of the therapeutic layer on the balloon surface by controlling the formation conditions of the therapeutic layer. This is important because morphology of the drug can have a significant impact on drug release, dissolution and uptake of the drug product. The dissolution rate of drug is mainly determined by surface-to-volume ratio of the particles/crystals formed on the surface of the balloon. By controlling the formation conditions of therapeutic layer, well-patterned morphologies such as a layer of needle crystals, a layer of particles formed by needle crystals, a layer of nanoparticles, a layer of microparticles and mixtures thereof can be achieved. In this context it is noted that it has been surprisingly found that the formation of a film, where the drug is essentially in a film form rather than in particulate form is undesirable because it may lead to the loss of large patches of the drug-coating, either en route to the desired site of action or following deployment at the site of action. As such, the use of both the adhesion balance layer and controlled formation of particles of drug on the surface of the balloon (in combination with a carrier material) is surprisingly effective in controlling the dissolution of the drug, and is also effective in preventing the loss of large particles, particle aggregates or patches of drug coating, which could potentially result in the blockage of a lumen of the body, for example, a subject's vascular capillary system, causing a distal embolization.

Hence, in embodiments of the invention, a drug coated balloon catheter coated with the adhesion balance layer and therapeutic layer may enable sufficient, uniform and rapid release of the therapeutic agent to reduce stenosis/restenosis in a target tissue.

Thus, there is provided a drug-coated medical device comprising:
- a balloon having an inner surface and an outer hydrophobic surface;
- an adhesion balance layer directly on the outer hydrophobic surface of the balloon, comprising a hydrophilic polymer and/or a hydrophilic compound where the hydrophilic compound has a molecular weight of less than 1,000 Daltons; and
- a therapeutic layer directly on the adhesion balance layer comprising a therapeutic agent and a pharmaceutically acceptable carrier, wherein:
- the therapeutic agent is a hydrophobic therapeutic agent with one or more hydrogen-bonding groups and is provided as discrete drug particles in the therapeutic layer;
- the drug particles have at least one dimension that is less than 25 µm and are uniformly distributed on the surface of the balloon; and
- the pharmaceutically acceptable carrier is hydrophilic and has a molecular weight of less than 1,000 Daltons.

As will be apparent, the medical device mentioned herein may be a catheter balloon for a balloon catheter or may be a balloon catheter. In each case, the coated component relates to the balloon.

The balloon is coated on the outer surface of the balloon with a layer that comprises small hydrophilic molecules and/or a hydrophilic polymer. This coating may also be referred to herein as the "adhesion balance layer". Without wishing to be bound by theory, it is speculated that the adhesion balance layer binds strongly to both the balloon surface and the therapeutic layer in the dry state, but when the adhesion balance layer absorbs water during transit and delivery its adherence falls, thereby allowing rapid release and transfer of an effective amount of the therapeutic agent to the target vessel when the balloon is inflated at the target site. Thus, by controlling the water absorption capability of the adhesion balance layer, the loss of adherence provided by the adhesion balance layer can be controlled and so the loss and release of drug particles in a drug-coated balloon comprising the adhesion balance layer and a uniformly distributed therapeutic layer (drug and carrier) can be tuned to effectively minimise drug loss and drug transfer.

As discussed hereinbefore, the problem with the use of balloon catheters to deliver therapeutic agents to the site of action is that it is difficult to strike a balance between drug adherence (during transit) and effective drug transfer (at the site of action). The drug-coated balloon catheter or balloon catheter of the present invention has a stable coating, hence reducing drug loss during handling and delivery to the target site. It is speculated that the hydrophilicity of the adhesion balance layer helps to improve the wetting of the therapeutic layer and hence provides a more uniform coating of therapeutic agent. Given this lower drug loss and more uniform coating morphology, the balloon of the current invention ensures a more consistent and predictable treatment, as well as a reduced risk of distal embolization and systemic toxicity. Without wishing to be bound by theory it is believed that the properties of the adhesion balance layer provide these good effects, in that the adhesion balance layer adheres strongly to the balloon and active substance (therapeutic) layer when dry and then swells (i.e. absorbs water) when in contact with water, hence effectively releasing the active substance layer onto the vessel wall. This enables efficient drug transfer to the vessel wall, reducing the need for a high drug dose on the device to achieve a therapeutic dose.

When used herein, the terms "hydrophilic" and "hydrophobic" refer to a substance that swells (i.e. absorbs water) or does not swell/contracts (i.e. does not absorb water) in the presence of water, respectively. Additionally or alternatively, when used herein, the terms "hydrophilic" and "hydrophobic" relate to the hydrophilic-lipophilic balance (HLB) value calculated according to the Davies' Method using formula (1). A polymer is considered hydrophilic if the HLB>10, and hydrophobic if the HLB<10.

$$HLB = 7 + \sum_{i=1}^{m} H_i - n \times 0.475 \qquad (1)$$

where:
m is the number of hydrophilic groups in the molecule;
$H_i$ is the value of the $i^{th}$ hydrophilic groups (e.g. based upon the tables provided by Davies); and
n is the number of lipophilic groups in the molecule.

When used herein, the term "comprising" is intended to require all components mentioned to be present, but to allow further components to be added. It will be appreciated that the term "comprising" also covers the terms "consisting of" and "consisting essentially of" as subsets, which are limited to only the components mentioned or to only the component mentioned along with some impurities, respectively. For the avoidance of doubt, it is explicitly contemplated that every use of the word "comprising" may be replaced with "consisting of" and "consisting essentially of" and variants thereof.

The balloon catheter of the present invention may be capable of immediate release of the active agent contained on its surface when it reaches the desired site of action in the tissue of a subject. Further, the dose provided by the balloon catheter may be a sustainable therapeutically effective amount. When used herein, the term "immediate release" means release from the balloon surface in a short period of time ranging from 1 second to 2 minutes, for example from 30 seconds to 1 minute. When used herein, the term "sustainable therapeutically effective amount" means a therapeutical or preventive effect against a disease or condition (e.g. stenosis/restenosis) of the treated tissue (e.g. a vascular tissue) for a period of up to 28 days.

Figure 2:
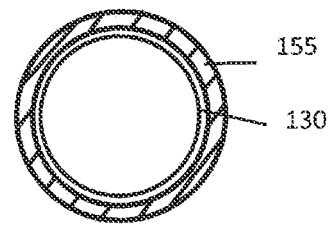
FIG. 2 depicts a cross-section of a prior art/comparative example drug coating on a balloon catheter, the coating having a single film layer that includes a therapeutic agent.

FIG. 1 (prior art) depicts a cross-sectional view of a balloon 130 coated with a single film layer 150 that includes a therapeutic agent and a carrier. FIG. 2 (prior art) depicts a cross-sectional view of a balloon 130 coated with a single film layer 155 that only contains a therapeutic agent. As noted above, problems associated with such coatings include the loss of drug before it reaches the desired site of action, and/or too little uptake of the drug once at the site of action, and/or release of large drug patches or particles to cause microvessel embolization. These problems make it difficult to provide any degree of certainty of providing a uniform delivery of drug from balloon to balloon, whether from the same manufacturing batch or from different manufacturing batches.

Figure 3:
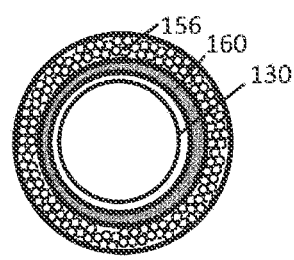
FIG. 3 depicts a cross-section of a drug coating on a balloon catheter according to an embodiment of the current invention, the coating having two layers, one being adhesion balance layer and the other being a well-controlled particle layer that includes a therapeutic agent and a carrier.

FIG. 3 depicts a cross-section of a balloon 130 according to the current invention, wherein the balloon has two layers 156 and 160. Layer 160 being an adhesion balance layer comprising a hydrophilic polymer and/or a hydrophilic compound (i.e. less than 1000 Daltons) that is placed directly onto the outer surface of balloon 130, and a therapeutic layer 156, which contains a therapeutic agent and a carrier, where the therapeutic agent is in the form of uniform particles with a desirable size (i.e. less than 25 µm in at least one dimension).

Figure 4:
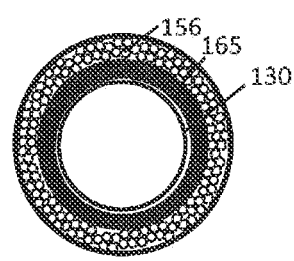
FIG. 4 depicts a cross-section of a drug coating on a balloon catheter according to an embodiment of the current invention, the coating having two layers, one being adhesion balance layer including a therapeutic agent and the other being a well-controlled particle layer that includes a therapeutic agent and a carrier.

FIG. 4 depicts a cross-section of a balloon 130 according to the current invention, wherein the balloon has two layers 156 and 165. Layer 165 being an adhesion balance layer comprising a hydrophilic polymer and/or a hydrophilic compound (i.e. less than 1000 Daltons) and a therapeutic agent that is placed directly onto the outer surface of balloon 130, and a therapeutic layer 156, which contains a therapeutic agent and a carrier, where the therapeutic agent is in the form of uniform particles with desirable size (i.e. less than 25 µm in any one dimension, for example less than 25 µm in any one (i.e. any) dimension).

The thickness of the adhesion balance layer in FIGS. 3 and 4 may be from 0.01 to 10 µm (e.g. from 0.01 to 4 µm, such as from 0.1 to 2 µm) when measured in a dry state.

The hydrophilic polymer and/or a hydrophilic compound (i.e. less than 1000 Daltons) used in the polymer layer of the balloons of the current invention may be provided in the form of a layer on the balloon surface that absorbs water (i.e. swells) when in contact with water (e.g. water in blood). In additional or alternative embodiments of the invention, the hydrophilic polymer and/or a hydrophilic compound (i.e. less than 1000 Daltons) may have a HLB that is greater than 10. It will be appreciated that the hydrophilic polymer and/or a hydrophilic compound in the adhesion balance layer contains hydrogen bonding moieties. Without wishing to be bound by theory, it is speculated that it is the presence of these moieties that enable the adhesion balance layer to provide the good effects noted herein.

Hydrophilic compounds that may be used to form the adhesion balance layer include one or more selected from the group consisting of a sugar, a sugar alcohol, and polyethylene glycol. The molecular weight of the hydrophilic compound used herein may be less than 1000 Daltons. When the compound is in the form of a polymeric material (or oligomeric material), then reference to molecular weight should be taken to be a reference to number average molecular weight. Particular hydrophilic compounds that may be used to form the adhesion balance layer include may be selected from one or more of the group consisting of fructose, glucose, sucrose, lactose, maltose, erythritol, threitol, arabitol, ribitol, mannitol, galactitol, fucitol, iditol, inositol, volemitol, isomalt, maltitol, lactitol, maltotriitol, maltotetraitol, xylitol, sorbitol and polyethylene glycol. More particular hydrophilic compounds that may be used to form the adhesion balance layer include may be selected from one or more of the group consisting of fructose, glucose, sucrose, xylitol, mannitol, and sorbitol.

Hydrophilic polymers that may be mentioned herein include those selected from one or more of the group consisting of poly (lactams) (e.g. polyvinylpyrollidone (PVP)), polyurethanes, homo- and copolymers of acrylic and methacrylic acid, polyvinyl alcohol, polyvinylethers, polyethers, maleic anhydride-based copolymers, vinylamines, polyethyleneimines, poly (carboxylic acids), polyamides, polyanhydrides, polyphosphazenes, cellulosics (for example methyl cellulose, carboxymethyl cellulose, hydroxymethyl cellulose, and hydroxypropylcellulose), heparin, dextran, polysaccharides, polyesters, oligopeptides, oligonucleotides, and copolymers and derivatives thereof. Particular hydrophilic polymers that may be mentioned herein include those selected from one or more of the group consisting of polyanhydrides, polyphosphazenes, polytetrahydrofuran, polyamides (particularly polypeptides (for example proteins, collagens (e.g. collagen), albumin, fibrins (e.g. fibrin), and elastin), polyesters (for example, polylactides (e.g. polylactic acid (PLA)), polyglycolides (polyglycolide (PGA)), poly (lactic-co-glycolic acid) (PLGA), poly (dioxanone) (PDO, PDS) and polycaprolactones (e.g. polycaprolactone (PCL)), polysaccharides (for example chitosan, starch, hyaluronic acid, alginates, gelatin, and chitin), or derivatives, co-polymers and mixtures of such, preferably PEG and its derivatives and co-polymers.

In certain embodiments of the invention, the hydrophilic polymer may be a polyether, a polyether derivative or a polyether copolymer. Polyethers that may be mentioned herein include paraformaldehyde, polyethylene glycol (PEG), polypropylene glycol (PPG), polytetramethylene glycol (PTMG) or their high molecular weight forms polyoxymethylene (POM), polyethylene oxide (PEO), polypropylene oxide (PPOX), polytetrahydrofuran (PTHF), respectively, as well as derivatives thereof and copolymers thereof. In particular embodiments of the invention, the polyether may be selected from one or more of polyethylene glycol/polyethylene oxide (PEO), polyethylene glycol/polyethylene oxide (PEO) derivatives, and polyethylene glycol/polyethylene oxide (PEO) copolymers thereof.

When used herein, the terms "polyethylene glycol/polyethylene oxide (PEO) derivatives, and polyethylene glycol/polyethylene oxide (PEO) copolymers thereof", may refer to one or more of the group consisting of diblock copolymers (for example PEG-PLA, PEG-PLGA, PEG-PCL), tri-block copolymers (for example PEG-PPG-PEG, PPG-PPG-PEG, PLA-PEG-PLA, PLGA-PEG-PLGA, PCL-PEG-PCL, PGA-PEG-PGA), multi-block copolymers (for example PEG-PPG-PEG), random copolymers, monofunctional PEGs (for example poly (ethylene glycol) methyl ether 2-bromoisobutyrate, poly (ethylene glycol) methyl ether acetylene, poly (ethylene glycol) methyl ether acrylate, methoypolyethylene glycol azide, methoxypolyethylene glycol amine, methoxypolyethylene glycol maleimide), homobifunctional PEGs (for example poly (ethylene glycol) bis (2-bromoisobutyrate), poly (ethylene glycol) diacetylene, poly (ethylene glycol) dimethyl ether, poly (ethylene glycol) bis (amine), poly (ethylene glycol) bisazide, poly (ethylene glycol) diglycidyl ether), heterobifunctional PEGs (for example amine PEG carboxyl, t-boc amine PEG amine), and methoxy PEGs (for example methoxy PEG succinimidylcarboxymethyl ester, methoxy PEG succinimidyl carbonate, methoxy PEG thiol, methoxy PEG amine). When mentioned in the above paragraph "PEG" may be replaced by "PEO".

In embodiments of the invention, the hydrophilic polymer may have a number average molecular weight of from 10,000 to 10,000,000 Daltons, such as from 100,000 to 5,000,000 Daltons, for example, from 500,000 to 2,000,000 Daltons.

Polyethylene glycol and polyethylene oxide may be referred to interchangeably as they relate to the same type of polymer. Polyethylene glycol typically refers to a polymer having a number average molecular weight of less than or equal to 20,000 Daltons and polyethylene oxide typically refers to a polymer having a number average molecular weight of greater than 20,000 Daltons. However, it will be understood that in embodiments of this invention these terms may be used interchangeably and are intended to cover all molecular weights noted above. This also applies to the other hydrophobic polymers that are mentioned herein.

In yet further embodiments of the invention, the adhesion balance layer may further comprise a hydrophobic polymer. In further embodiments of the invention, the hydrophobic polymer may be a polymer that does not swell when in contact with water. In additional or alternative embodiments of the invention, the hydrophilic polymer may have a HLB that is less than 10. Examples of hydrophobic polymers that may be mentioned herein may be selected from one or more of the group consisting of polyanhydrides, polyethers (for example poly (propylene glycol) (PPG), polytetrahydrofuran (polyTHF)), polyesters (for example polylactic acid (PLA), poly (dioxanone) (PDO, PDS), polycaprolactone (PCL), polyglycolide (PGA), poly (lactic-co-glycolic acid) (PLGA), polyhydroxybutyrate (PHB)), polysaccharides (for example starch), and derivatives, co-polymers and mixtures thereof.

In certain embodiments of the invention, the adhesion balance layer may contain less than 30 wt % of the hydrophobic polymer. In embodiments of the invention, the hydrophilic polymer and/or hydrophobic polymer may not be shellac.

In yet further embodiments of the invention, the hydrophilic polymer may be a block copolymer comprising hydrophobic and hydrophilic blocks. The molecular weight of the block copolymer is as provided above for the hydrophobic polymer. In certain embodiments that may be mentioned herein, the hydrophobic polymer and the hydrophobic polymer blocks may be less than a total of 30 wt % of the polymer layer.

In embodiments of the invention, the therapeutic agent in the therapeutic agent layer may be selected from one or more of the group consisting of an antiproliferative, immunosuppressive, anti-angiogenic, anti-inflammatory, and anti-thrombotic agent. For example, the therapeutic agent may be selected from one or more of the group consisting of paclitaxel, rapamycin, everolimus, zotarolimus, umirolimus, tacrolimus, and pimecrolimus (e.g. selected from one or more of the group consisting of paclitaxel, rapamycin, zotarolimus and umirolimus). In particular embodiments of the invention, the therapeutic agent may be paclitaxel.

In yet further embodiments of the invention, the adhesion balance layer may further comprise a therapeutic agent, optionally wherein the therapeutic agent may be selected from an antiproliferative, immunosuppressive, anti-angiogenic, anti-inflammatory, and anti-thrombotic agent. For example, the therapeutic agent may be selected from one or more of the group consisting of paclitaxel, rapamycin, everolimus, zotarolimus, umirolimus, tacrolimus, and pimecrolimus (e.g. selected from one or more of the group consisting of paclitaxel, rapamycin, zotarolimus and umirolimus). In particular embodiments of the invention, the therapeutic agent may be paclitaxel. When referred to herein, the "therapeutic agent" is a hydrophobic therapeutic agent which nevertheless possesses one or more hydrogen bonding groups.

As noted hereinbefore, the therapeutic agent layer comprises a pharmaceutically acceptable carrier. The pharmaceutically acceptable carrier may be selected from one or more of the group consisting of tartaric acid, a sugar, and a sugar alcohol. In particular embodiments of the invention, the pharmaceutically acceptable carrier may be selected from one or more of the group consisting of fructose, glucose, sucrose, lactose, maltose, erythritol, threitol, arabitol, ribitol, mannitol, galactitol, fucitol, iditol, inositol, volemitol, isomalt, maltitol, lactitol, maltotriitol, maltotetraitol, more particularly, xylitol, tartaric acid, and sorbitol. As noted hereinbefore, the carrier has a molecular weight of less than 1000 Daltons. When the carrier is a polymer, reference to molecular weight is a reference to the number average molecular weight. When used herein, the amount of carrier to therapeutic agent in the therapeutic layer may be from 1:8 to 8:1 wt/wt (e.g. from 1:4 to 3:1 wt/wt).

In embodiments of the invention, the therapeutic agent may be present in a total loading on the balloon of from 1 μg/mm$^2$ to 10 μg/mm$^2$ (e.g. from 1.5 μg/mm$^2$ to 4 μg/mm$^2$, such as from 2 μg/mm$^2$ to 3 μg/mm$^2$). Said total loading may be determined as the total loading of the therapeutic agent in the therapeutic layer and (in certain embodiments) in the adhesion balance layer.

As mentioned hereinbefore, the use of a hydrophilic carrier material in combination with the hydrophobic therapeutic agent may prevent the formation of aggregates of the drug particles and the like. As such, the drug particles may have a size that is less than 25 μm in at least one dimension (e.g. less than 15 μm or less than 10 μm). It will be appreciated that the drug particles may have a size that is less than 25 μm in any one (i.e. all) dimension (e.g. less than 15 μm or less than 10 μm in any one dimension).

Figures 10A, 10B:
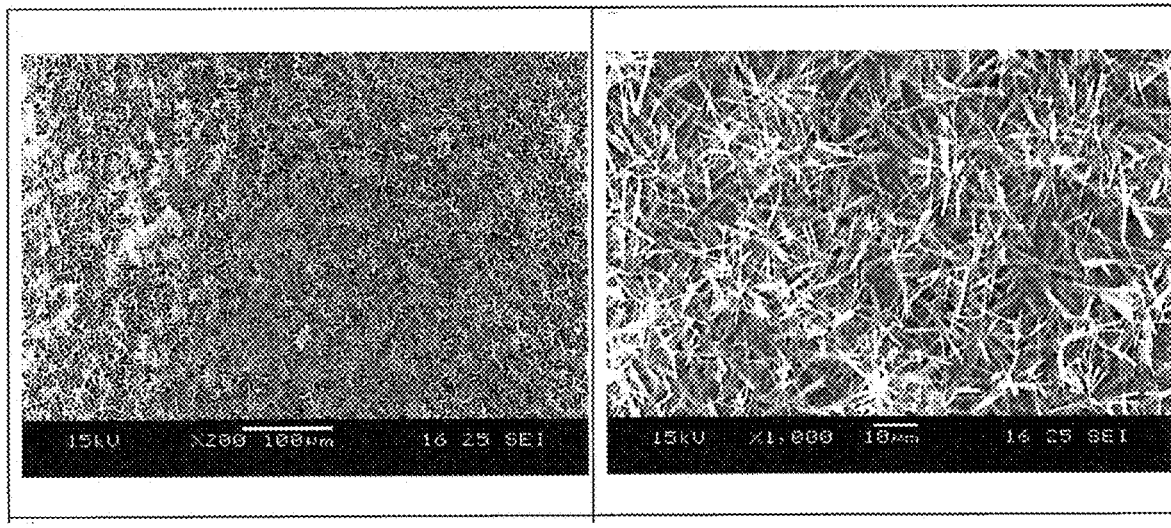
FIGS. 10A-10D provide SEM images of coating morphology on balloons of the current invention.
Figures 10C, 10D:
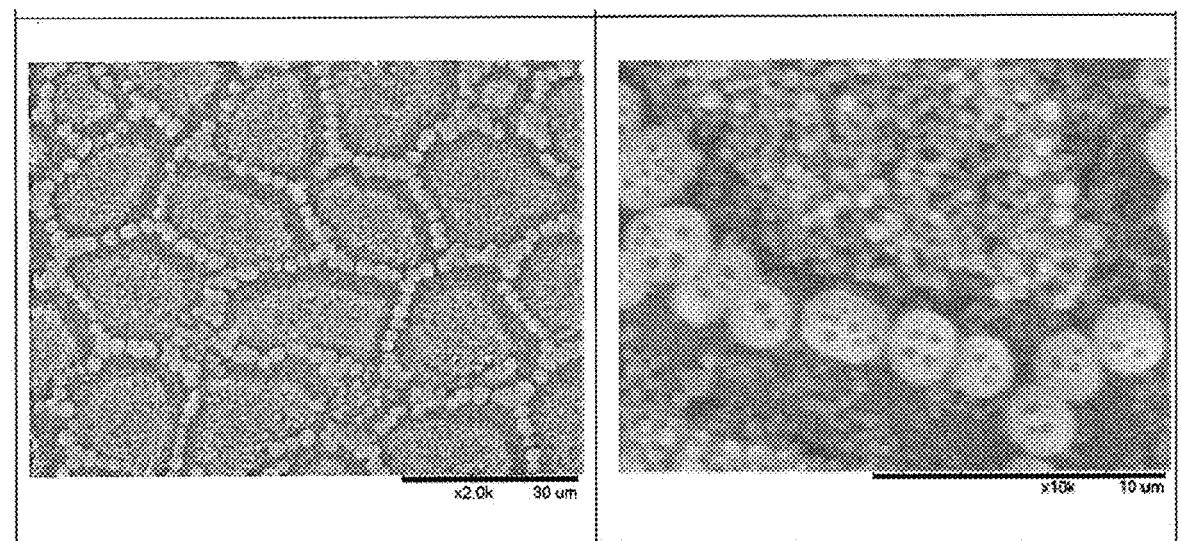
Figure 12:
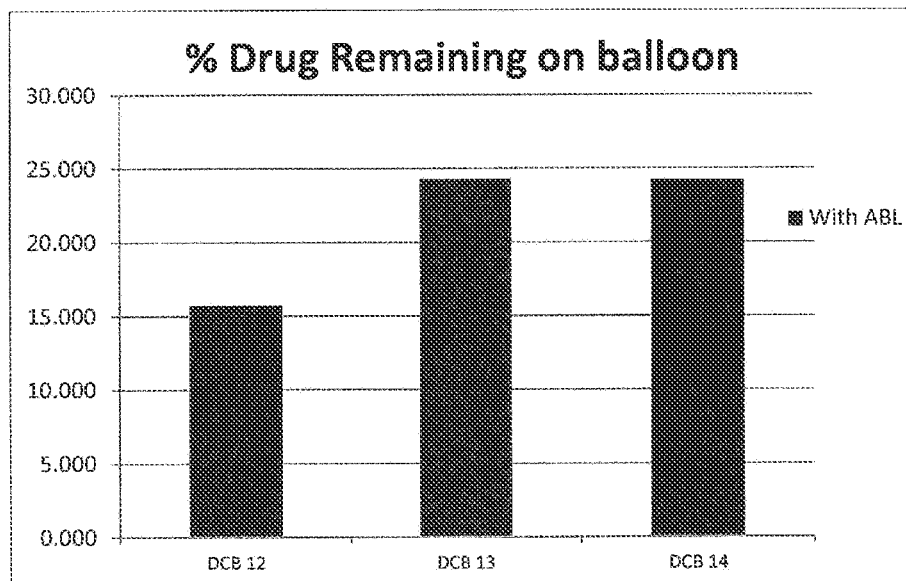
FIG. 12 is a graph comparing the in vitro drug remaining on the balloon following deployment in respect of balloons of the current invention and comparative examples (DEB12-14).
Figure 13:
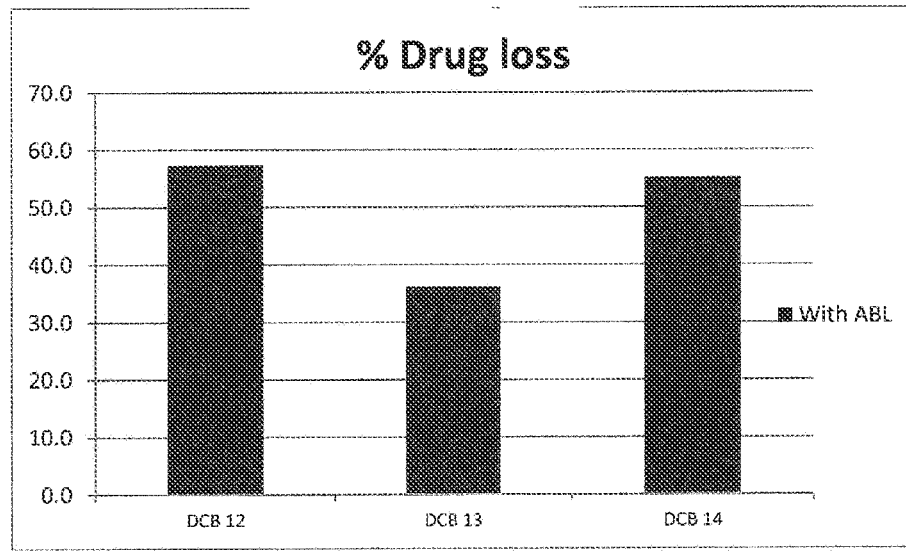
FIG. 13 is a graph comparing the in vitro transit drug loss in respect of balloons of the current invention and comparative examples (DEB12-14).
Figure 14:
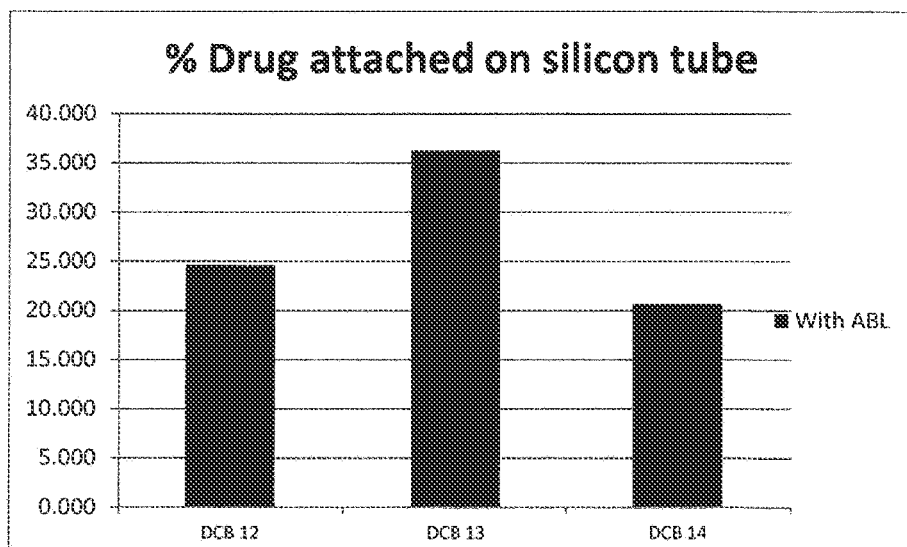
FIG. 14 is a graph comparing the in vitro drug uptake in respect of balloons of the current invention and comparative examples (DCB 12-14)

The drug particles may be distributed evenly over the surface of the balloon. As noted hereinbefore, the drug particles may take the form of one or more of the group selected from particulate needles, microparticles and nanoparticles. In certain embodiments that may be mentioned herein, the drug particles may be provided in the form of "cells" where microparticles provide a multiplicity of vesicle-like two-dimensional structures, where the vesicle is at least partially filled by nanoparticles (e.g. see FIGS. 10 C and D).

In embodiments of the invention, wherein the therapeutic and adhesion balance layers may provide a uniform coating over the outer surface of the balloon, optionally wherein the uniform surface is interrupted by lines caused by folds in the balloon.

In yet further embodiments of the invention, the catheter balloon may form an integral or removable part of a balloon catheter.

The drug-coated medical device described hereinbefore may be prepared by:

(a) providing an uncoated balloon;

(b) providing an adhesion balance layer precursor mixture, coating at least part of the outer surface of balloon with the adhesion balance layer precursor mixture to form an adhesion balance layer precursor layer and drying the adhesion balance layer precursor layer to provide a balloon coated with an adhesion balance layer;

(c) providing a therapeutic agent mixture and coating the therapeutic agent solution onto the outer surface of the balloon coated with an adhesion balance layer, followed by drying the coated balloon to provide the drug-coated catheter balloon, wherein therapeutic agent mixture comprises a hydrophobic therapeutic agent with one or more hydrogen-bonding groups, a solvent and a hydrophilic pharmaceutically acceptable carrier that has a molecular weight of less than 1,000 Daltons; and the adhesion balance layer precursor mixture comprises a hydrophilic polymer and/or a hydrophilic compound, where the hydrophilic compound has a molecular weight of less than 1,000 Daltons.

The hydrophobic therapeutic agent, the hydrophilic pharmaceutically acceptable carrier, the hydrophilic polymer and the hydrophilic compound mentioned above are intended to be the same as those described hereinbefore in relation to the coated medical device.

It will be appreciated that the balloon used herein may be provided in a folded state and so may be coated in this folded state. Alternatively, the process may further comprise the steps of:

(i) inflating the balloon between step (a) and (b), optionally wherein the inflation is to a pressure of 2 atm ($2.0265 \times 10^5$ P);

(ii) deflating the balloon following step (c); and (iii) folding the balloon following step (ii).

As noted above, the balloon can be coated in a deployed and inflated condition, or by coating the balloon under the folds in a folded condition.

In embodiments of the invention, the adhesion balance layer precursor mixture may comprise the hydrophilic polymer and/or the hydrophilic compound in combination with a solvent selected from one or more of the group consisting of water, acetone, acetonitrile or a $C_{1-4}$ alcohol (e.g. a non-limiting $C_{1-4}$ alcohol that may be mentioned herein is ethanol). The hydrophilic polymer may be present at a concentration of from 0.167 mg/mL to 20 mg/mL (e.g. from 0.2 mg/mL to 20 mg/mL) in the adhesion balance layer precursor mixture. In certain embodiments, the adhesion balance layer precursor mixture may further comprise a hydrophobic polymer, the kind and amount of the hydrophobic material used herein is hereinbefore described in relation to the medical device.

In yet further embodiments of the invention, the therapeutic agent mixture may comprise a therapeutic agent and a solvent selected from one or more of the group consisting of dichloromethane, or more particularly, water, acetone, acetonitrile, tetrahydrofuran (THF) or a $C_{1-4}$ alcohol (e.g. ethanol or methanol), optionally wherein the therapeutic agent is present at a concentration of from 5 mg/mL to 100 mg/ml in the therapeutic agent mixture.

The hydrophilic carrier may be one or more of those described hereinbefore in relation to the medical device. The carrier may be present at a concentration of from 0.5 mg/mL to 100 mg/ml (e.g. from 10 mg/mL to 50 mg/mL, such as from 20 mg/mL to 25 mg/mL) in the therapeutic agent mixture.

The therapeutic agent of the therapeutic agent layer may be selected from one or more of the group consisting of an antiproliferative, immunosuppressive, anti-angiogenic, anti-inflammatory, and anti-thrombotic agent (e.g. the therapeutic agent may be selected from one or more of the group consisting of paclitaxel, rapamycin, everolimus, zotarolimus, umirolimus, tacrolimus, and pimecrolimus (such as a therapeutic agent selected from one or more of the group consisting of paclitaxel, rapamycin, zotarolimus and umirolimus, such as paclitaxel and rapamycin)). The therapeutic agent may be present at a concentration of from 0.5 mg/mL to 100 mg/mL (e.g. from 20 mg/mL to 80 mg/mL, such as from 35 mg/mL to 65 mg/mL) in the therapeutic agent mixture.

In certain embodiments, the coating of steps (b) and (c) may be accomplished by one or more of the group consisting of brush coating, spraying, dipping syringe depositing or pipette depositing. For example, the coating of step (b) is accomplished by dip coating, and/or the coating of step (c) is accomplished by spray coating.

Figures 9A, 9B:
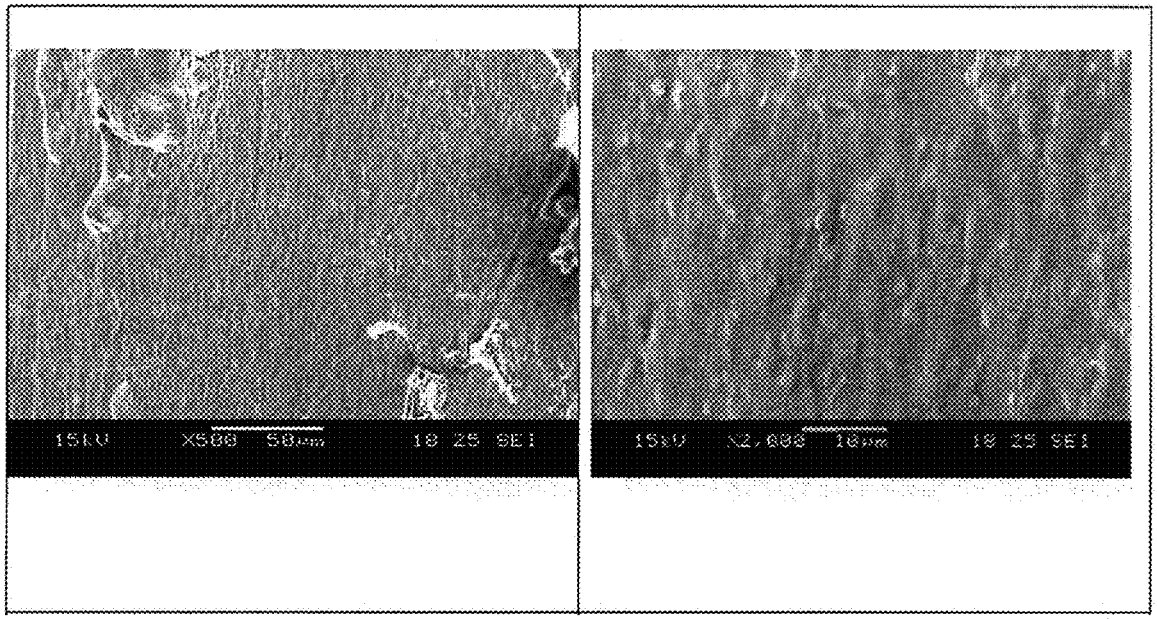
FIGS. 9A-9D provide SEM images of coating morphology on balloons of the current invention.
Figures 9C, 9D:
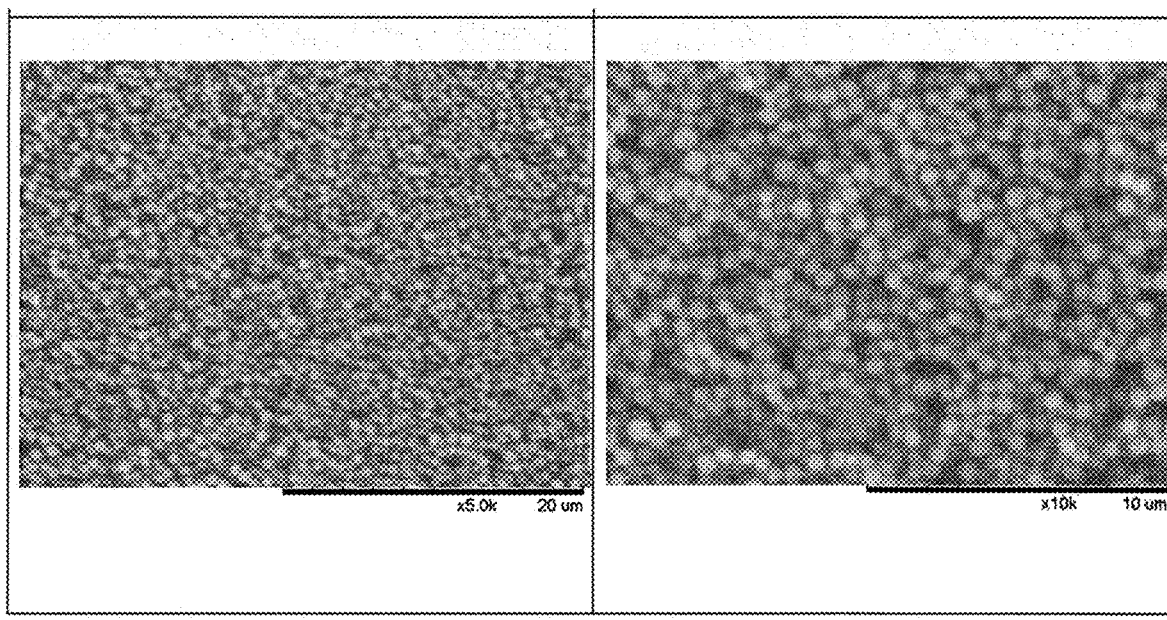

In embodiment of the invention, the drying temperature of step (c) of the process described hereinbefore can be controlled to achieve morphologies like a layer of needle crystals, a layer of particles formed by needle crystals, a layer of nanoparticles, a layer of microparticles and their mixtures can be achieved (e.g. see FIGS. 9 and 10). For example, the temperature used in step (c) may be in the range of from 30° C. to 100° C., such as from 35° C. to 80° C., from 40° C. to 60° C. (e.g. 45° C.).

In certain embodiments of the process, the medical device may be a balloon catheter and the balloon may be integrally formed as part of a balloon catheter. In alternative embodiments, the process may further comprise fixing the balloon onto a balloon catheter either as a removable or integral part of said balloon catheter to form the medical device.

As will be appreciated, the balloon of the current invention is provided with a coating of a consumable drug. As such, the drug-coated medical device described hereinbefore may be used in medicine. That is, there is provided a use of a drug-coated medical device according to the first aspect of the invention, and any technically sensible combination of embodiments thereof, for use in medicine.

In aspects of the invention, there is provided:

(a) a method of treatment using a drug-coated medical device as described hereinbefore to deliver a drug to a tissue in need of said treatment;

(b) a drug-coated medical device as described hereinbefore for use in the delivery of a drug to a tissue in need of said treatment; and (c) use of a drug-coated medical device as described hereinbefore in the preparation of a medicament for use in the delivery of a drug to a tissue in need of said treatment.

In embodiments of the invention the use/delivery of an active agent may be to treat or prevent stenosis or restenosis, optionally using one or more of the therapeutic agents mentioned herein. In further embodiments, the tissue to be treated may be a hollow tissue (e.g. a tissue with a lumen). Particular tissues that may be mentioned herein include vascular tissues.

In certain embodiments of the invention, the method of treatment of a subject may comprise the steps of:

(a) inserting the drug-coated medical device into a hollow tissue of a subject;
(b) advancing the medical device to a target site in a tissue;
(c) inflating the balloon and maintaining the inflated state for a period of time sufficient for the therapeutic agent to adhere to the target site;
(d) deflating the balloon and removing the medical device from the subject.

In certain embodiments, period of time may be from 1 second to 2 minutes, such as from 30 seconds to 1 minute.

EXAMPLES

General Preparation 1

Adhesion Balance Layer Precursor Mixtures (ABL)
The ABL_solutions were prepared by adding the indicated ingredients together and mixing using conventional means. Details are provided in Table 1 below.

TABLE 1

| Generic ABL No. | Polymer and optional additives | Solvent |
| --- | --- | --- |
| 1 | PVP (1-10 mg) | Water, ethanol or mixtures thereof (a total solvent amount of from 1 mL to 6 mL) |
| 2 | PEG (1-10 mg) | Water, ethanol or mixtures thereof (a total solvent amount of from 1 mL to 6 mL) |
| 3 | Sorbitol (1-10 mg) | Water, ethanol or mixtures thereof (a total solvent amount of from 1 mL to 6 mL) |
| 4 | Xylitol (1-10 mg); Paclitaxel (50-100 mg) | Water, ethanol or mixtures thereof (a total solvent amount of from 1 mL to 6 mL) |
| 5 | Glucose (1-10 mg) | Water, methanol or mixtures thereof (a total solvent amount of from 1 mL to 6 mL) |
| 6 | PEG (1-10 mg) | Acetonitrile, or a mixture of acetonitrile and water (a total solvent amount of from 1 mL to 6 mL) |
| 7 | Sucrose (1-10 mg) | Water, methanol or mixtures thereof (a total solvent amount of from 1 mL to 6 mL) |
| 8 | PEG (1-10 mg) | Water, acetone or mixtures thereof (a total solvent amount of from 1 mL to 6 mL) |
| 9 | Glucose (1-10 mg) | Water, acetone or mixtures thereof (a total solvent amount of from 1 mL to 6 mL) |

General Preparation 2

Therapeutic Agent Mixtures (TAM)
The TAM solutions were prepared by adding the indicated ingredients together and mixing using conventional means. Details are provided in table 2 below.

TABLE 2

| Generic TAM Solution No. | Therapeutic agent and optional carrier | Solvent |
| --- | --- | --- |
| 1 | Rapamycin (50-100 mg) | Acetone (1 mL to 6 mL) |
| 2 | Paclitaxel (50-100 mg); carrier (10-50 mg) | Acetonitrile or ethanol (1 mL to 6 mL) |
| 3 | Paclitaxel (50-100 mg) | Acetonitrile or ethanol (1 mL to 6 mL) and water (0.1 to 3 mL) |
| 4 | Paclitaxel (50-100 mg); carrier (10-50 mg) | Acetonitrile (1 mL to 6 mL) and water (0.1 to 3 mL) |
| 5 | Rapamycin (50-100 mg); carrier (10-50 mg) | Methanol or ethanol (1 mL to 6 mL) |
| 6 | Paclitaxel (50-100 mg); carrier (10-50 mg) | Methanol or ethanol (1 mL to 6 mL) |
| 7 | Rapamycin (50-100 mg) | Acetone (1 mL to 6 mL) |
| 8 | Paclitaxel (50-100 mg) | Acetone or ethanol (1 mL to 6 mL) and water (0.1 to 3 mL) |

General Preparation 3

Coating a Balloon with TAM Only
The following steps were followed:
1) a folded uncoated balloon was provided;
2) said balloon was inflated to 2 atm using air;
3) a solution of one of TAM 1-8 from General Preparation 2 was applied onto the surface of the balloon of step (2) to give a dose of 3 µg/mm$^2$, and the coated balloon surface was then dried;
4) the balloon of step (3) was deflated; and
5) the deflated balloon of step (4) was folded in preparation for use.

The coating and application in step (3) were accomplished by conventional coating methods such as brush coating or, more particularly, by spraying, dipping, syringe depositing or pipette depositing.

The drying step in (3) can be performed at room temperature or at elevated temperatures and at atmospheric pressure or under reduced pressure.

General Preparation 4

Coating a Balloon with ABL and TAM
1) a folded uncoated catheter balloon was provided;
2) said balloon was inflated to 2 atm using air;
3) one of ABL 1-9, as described in General Procedure 1, was applied to the surface of the balloon of step (2), following which the coated balloon surface was dried;
4) a solution of one of TAM 1-8 from General Preparation 2 was applied onto the surface of the balloon of step (3) to give a dose of 3 µg/mm$^2$, and the coated balloon surface was then dried;
5) the balloon of step (4) was deflated; and
6) the deflated balloon of step (5) was folded in preparation for use.

The coating and applications conducted in steps (3) and (4) were accomplished by conventional coating methods were accomplished by conventional coating methods such as brush coating or, more particularly, by spraying, dipping syringe depositing or pipette depositing.

The drying step in (3) and (4) can be performed at room temperature or at elevated temperatures and at atmospheric pressure or under reduced pressure.

Example 1

The following TAM were prepared.
a) 70 mg of paclitaxel, 2 mL of ethanol, 50 mg of Sorbitol were mixed together.
b) 70 mg of paclitaxel, 2 mL of ethanol, 50 mg of Urea were mixed.

Balloons 1-2 (No Polymer Layer)

Balloons 1-2 were prepared according to General Preparation 3, where the therapeutic agent mixture is coated directly onto the surface of an uncoated catheter balloon. Details of the balloons are provided in table 3 below.

TABLE 3

| Balloon No. | TAM used |
| --- | --- |
| 1 | (a) |
| 2 | (b) |

The construction of balloons 1 and 2 correspond to FIG. 1.

Balloons 3-5 (Including Adhesion Balance Layer)

Balloons 3-5 were prepared according to General Preparation 4, where the ABL is coated directly onto the surface of an uncoated catheter balloon and the therapeutic agent mixture is coated on top of the resulting adhesion balance layer. Details of the balloons are provided in table 4 below.

TABLE 4

| Balloon No. | ABL used | TAM used |
| --- | --- | --- |
| 3 | 5 mg of PEG (number average molecular weight of 1,000,000 Daltons) was dissolved in 2 mL of 1:2 mixtures of ethanol and water. | (a) |
| 4 | 5 mg of glucose was dissolved in 2 mL of 1:2 mixtures of ethanol and water. | (b) |
| 5 | 5 mg of PEG (number average molecular weight of 1,000,000 Daltons) was dissolved in 2 mL of 1:2 mixtures of ethanol and water. | (b) |

The construction of balloons 3-5 correspond to FIG. 3. All test balloons (1-5) are 3 mm×15 mm.

Method

In-vitro testing methods were adapted from Seidlitz et al. (2013) In Vitro Determination of Drug Transfer from Drug-Coated Balloons *PLoS ONE* 8(12): e83992 (doi: 10.1371/journal.pone.0083992).

The following changes were made:
A silicon tube was used for the model vessel wall.
Imaging of the model vessel wall was not carried out, and thus the balloons were not treated with fluorescent substances.
Drug contents were extracted in acetonitrile (ACN) and analysed using UV-spectrometer at 227 nm.
Balloons were inflated to pressure of 12 atm.
Drug remaining on the balloon were then also analysed, so that the drug loss during introduction and transit of the balloon were also deduced.

Results

Figures 5A, 5B, 5C:
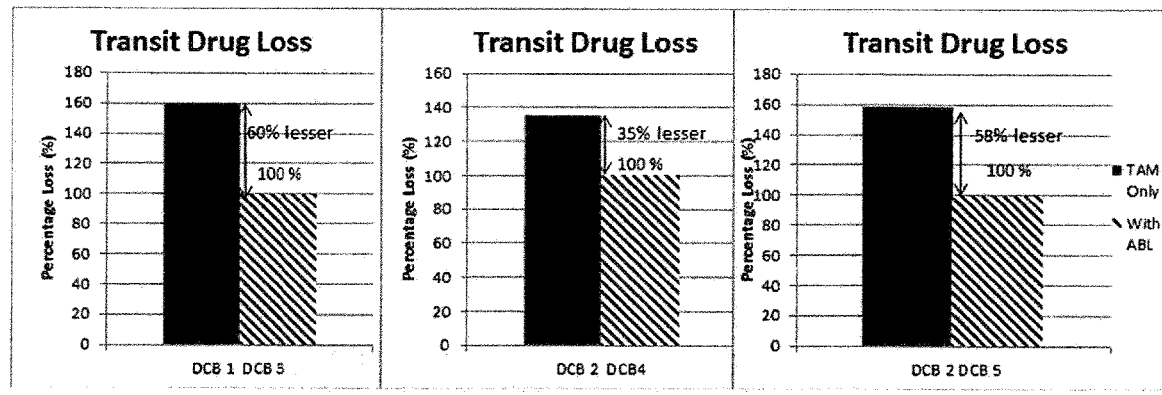
FIGS. 5A-5C are graphs comparing the in vitro drug loss in respect of balloons of the current invention and comparative examples.

As shown in FIGS. 5A-5C, the drug-coated balloons 3-5, which have the adhesion balance layer (i.e. a hydrophilic polymer, or a hydrophilic molecule of less than 1000 Daltons) between the balloon surface and the therapeutic layer, have significantly lower drug loss when compared to drug-coated balloons 1-2 that do not have the adhesion balance layer. This is true for all therapeutic layers with or without the addition of a carrier to the therapeutic layer. The results depicted in FIG. 5A-5C clearly show that the adhesion balance layer significantly improves the stability of the therapeutic coating.

Figures 6A, 6B, 6C:
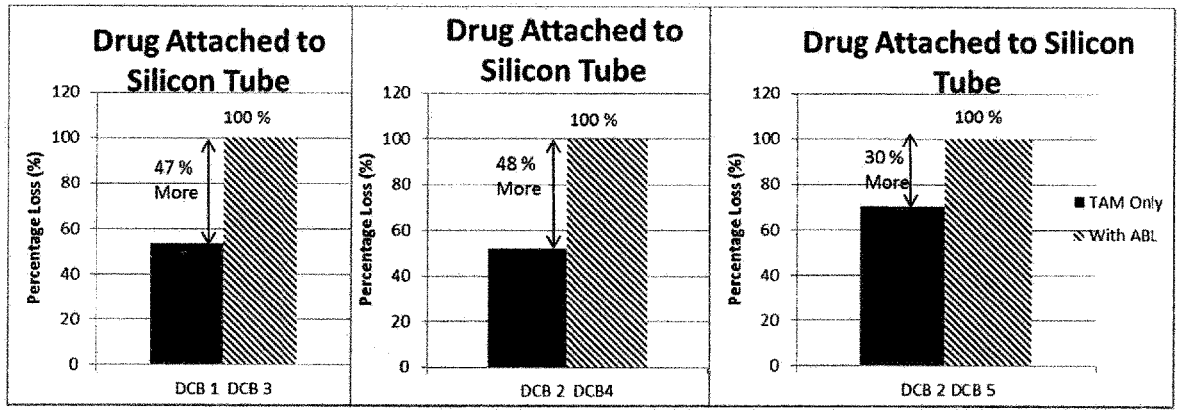
FIGS. 6A-6C are graphs comparing the in vitro drug uptake in respect of balloons of the current invention and comparative examples.

As shown in FIGS. 6A-6C, the drug-coated balloons 3-5, which have the adhesion balance layer between the balloon surface and the therapeutic layer, also resulted in up to 50% more drug uptake when compared to balloons without the adhesion balance layer (balloons 1-2), for all therapeutic layers with the addition of a carrier to the therapeutic layer. These results show that the addition of the adhesion balance layer reduces the loss of the drug en route to the desired target site and also improves drug uptake at the site of action too.

Example 2

Table 5 lists the balloons prepared for use in an in vivo test.

TABLE 5

| Balloon No. | ABL used | TAM used |
| --- | --- | --- |
| 6 | — | 70 mg of paclitaxel, 2 mL of ethanol, 50 mg of tartaric acid were mixed |
| 7 | 5 mg of PEG (number average molecular weight of 1,000,000 Daltons) was dissolved in 2 mL of 1:2 mixtures of ethanol and water. | 70 mg of paclitaxel, 2 mL of ethanol, 50 mg of tartaric acid were mixed |

Balloon 6 was prepared in accordance with the procedure provided in General Preparation 3 (the construction of balloon 6 corresponding to FIG. 2). Balloon 7 was prepared in accordance with the procedure provided in General Preparation 4 (the construction of balloon 7 corresponds to FIG. 3). All balloons were 3 mm×15 mm.

Samples were evaluated in an animal study. Seven New Zealand White rabbits of 3-4 kg body weight were included in the study in which 12 balloons each were deployed. The left and right iliac arteries of each animal were randomly assigned.

One group (group 1) of balloons were deployed to study the drug transfer of the coating while the other group (group 2) were deployed to study the amount of drug loss during transit.

Method

The study protocol was adapted from Granada J F, et al., Mechanisms of tissue uptake and retention of paclitaxel-coated balloons: impact on neointimal proliferation and healing. *Open Heart* (2014) August 6; 1 (1): e000117 (doi: 10.1136/openhrt-2014-000117. eCollection 2014).

Adaptions to the protocol given above for group 1 are as follows.

Rabbit iliac arteries were used instead of the abdominal aorta due to the smaller balloons used.

Only acute (5 minutes time point) data were collected.

The amount of drug remaining on the balloon was additionally analysed. The balloons were extracted in methanol and analysed by LC/MS.

For group 2, the drug-coated balloons were deployed in a similar procedure. However, the balloon was held in the iliac artery without inflation for 60 seconds. The balloon was then slowly removed, cut from the catheter, and kept for analysis.

Results

Figure 7:
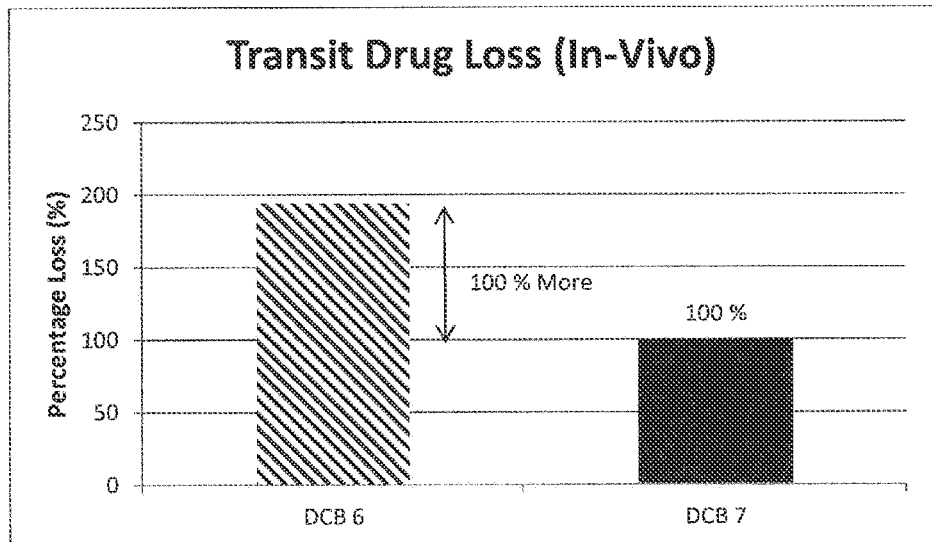
FIG. 7 is a graph comparing the in vivo drug loss in respect of balloons of the current invention and comparative examples.

As shown in FIG. 7, the drug-coated balloon 7, which has the adhesion balance layer (i.e. of a hydrophilic polymer, or hydrophilic molecule having a molecular weight of less than 1000 Daltons) between the balloon surface and the therapeutic layer, has close to 100% lower drug loss in the in-vivo study compared to balloon 6, which does not have the intermediate adhesion balance layer. This reflects the improved stability of the drug-coated balloon 7, having the intermediate adhesion balance layer, as observed during the previous in vitro laboratory tests described in Example 1.

Figure 8:
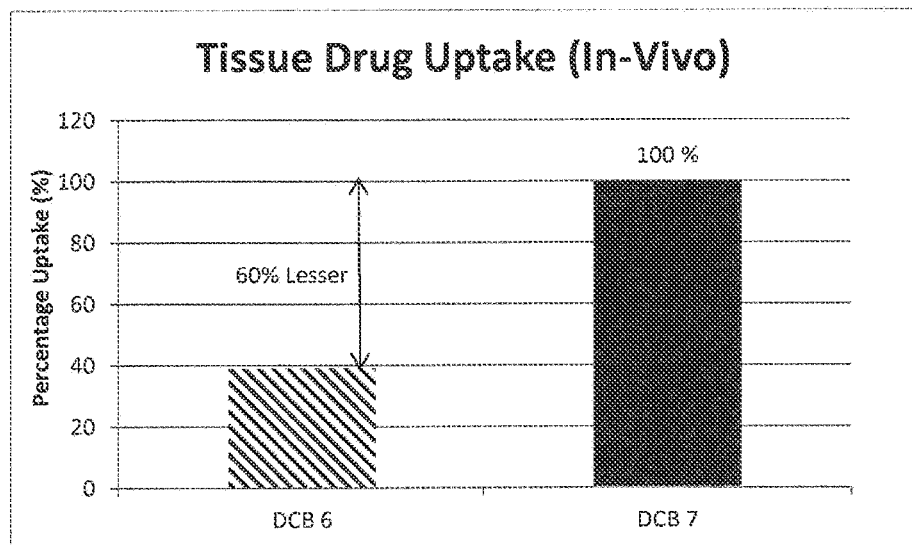
FIG. 8 is a graph comparing the in vivo drug uptake in respect of balloons of the current invention and comparative examples.

In addition, as shown in FIG. 8, about 60% more drug was transferred to the target vessel from balloon 7 samples compared to balloon 6 samples. This shows that the intermediate polymer layer not only improved the drug transfer efficiency of the drug-coated balloon, but greatly enhanced the dry adherence of the coating to the balloon, hence reducing drug loss.

Example 3

Table 6 lists the balloons prepared for use in an in vitro test. Balloons 8-11 were prepared according to General Preparation 4, where the ABL is coated directly onto the surface of an uncoated catheter balloon and the therapeutic agent mixture is coated on top of the resulting adhesion balance layer. The drying temperature of step 4 in general preparation 4 is also provided in Table 6 below. The testing method of in vitro drug loss and uptake is the same as those in Example 1.

TABLE 6

| Balloon No. | ABL used | TAM used | Drying temperature in General Preparation 4, step 4 (resulting form of particles) |
|---|---|---|---|
| 8 | 5 mg of PEG (number average molecular weight of 1,000,000 Daltons) was dissolved in 2 mL of 1:2 mixtures of ethanol and water. | 70 mg of paclitaxel, 2 mL of acetone were mixed | 25° C. (film; no particles) |
| 9 | 5 mg of PEG (number average molecular weight of 1,000,000 Daltons) was dissolved in 2 mL of 1:2 mixtures of ethanol and water. | 80 mg of paclitaxel, 2 mL of acetonitrile, 40 mg of tartaric acid were mixed | 45° C. (needle) |
| 10 | 5 mg of PEG (number average molecular weight of 1,000,000 Daltons) was dissolved in 2 mL of 1:2 mixtures of ethanol and water. | 100 mg of paclitaxel, 2 mL of acetone/water (w/w 8:2), 50 mg of tartaric acid were mixed | 45° C. (particle) |
| 11 | 5 mg of PEG (number average molecular weight of 1,000,000 Daltons) was dissolved in 2 mL of 1:2 mixtures of ethanol and water. | 120 mg of paclitaxel, 2 mL of acetone/water (w/w 8:2), 40 mg of tartaric acid were mixed | 45° C. (micro-nano) |

As shown in FIGS. 9A-9D and 10A-10D (pictures taken using a JEOL JSM-5600LV SEM), the drug-coated balloons 8-11 show different morphologies by changing the solvent, type of carrier, carrier concentration and drying temperature. The therapeutic layer of balloon 8 is dried at 25° C. and with no carrier, resulting in the formation of a film. The therapeutic layer of balloons 9-11 are dried at elevated temperature and with a higher carrier concentration and different solvent. These conditions tune the evaporation rate of solvent, which results in different structures, such as needle crystals (DEB9), nanoparticles (DEB10) and a micro particle/nanoparticle mixture (DEB11) on the surface. This indicates that surface morphology can be controlled through a combination of the coating formula employed (solvent, active, carrier and concentrations thereof in said solvent) and drying temperature at step (4) of the general preparation. It is worth mentioning that these morphologies can be achieved through any of dip coating, brush coating, spray coating or pipetting of the therapeutic layer.

Example 4

Table 7 lists the balloons prepared for use in an in vitro test. All balloons were prepared according to General Preparation 4. The testing method of in vitro drug loss and uptake is the same as those in Example 1.

TABLE 7

| Balloon No. | ABL used | TAM used | Comments |
|---|---|---|---|
| 12 | 5 mg of PEG (number average molecular weight of 1,000,000 Daltons) was dissolved in 2 mL of 1:2 mixtures of ethanol and water. | 50 mg of paclitaxel, 2 mL of ethanol, 50 mg of tartaric acid were mixed | Carrier to drug ratio is 1:1 |
| 13 | 5 mg of PEG (number average molecular weight of 1,000,000 Daltons) was dissolved in 2 mL of 1:2 mixtures of ethanol and water. | 50 mg of paclitaxel, 2 mL of ethanol, 100 mg of tartaric acid were mixed | Carrier to drug ratio is 2:1 |
| 14 | 5 mg of PEG (number average molecular weight of 1,000,000 Daltons) was dissolved in 2 mL of 1:2 mixtures of ethanol and water. | 50 mg of paclitaxel, 2 mL of ethanol, 200 mg of tartaric acid were mixed | Carrier to drug ratio is 4:1 |

As shown in FIGS. 11A-11D, 12 and 13, by varying the carrier to drug ratio, the drug uptake and drug loss can be optimized. Balloon 13, which is prepared from a carrier to drug ratio of 2:1, provides a higher drug transfer, lower drug remaining and lower drug loss than the rest of the samples. These results indicate that certain amount of carrier can balance the surface interaction between drug particles as well as the surface interaction between drug particles and the adhesion layer. If the carrier amount is too high, it will impact the stability of drug layer, which leads to high drug loss and low drug uptake.

It will be appreciated that the necessary factors affecting the performance of the drug-coating can be adjusted by a person skilled in the art to optimise the transfer following the teachings provided herein.

The invention claimed is:

1. A drug-coated medical device comprising:
   a balloon having an inner surface and an outer hydrophobic surface;
   an adhesion balance layer directly on the outer hydrophobic surface of the balloon, comprising a hydrophilic polymer and/or a hydrophilic compound, where the hydrophilic polymer has a number average molecular weight of from 10,000 to 10,000,000 Daltons and the hydrophilic compound is a sugar with a molecular weight of less than 1,000 Daltons; and
   a therapeutic layer directly on the adhesion balance layer comprising a therapeutic agent and a pharmaceutically acceptable carrier, wherein:
   the therapeutic agent is a hydrophobic therapeutic agent with one or more hydrogen-bonding groups and is provided as discrete drug particles in the therapeutic layer;
   the drug particles have at least one dimension that is less than 25 μm and are uniformly distributed on the surface of the balloon; and
   the pharmaceutically acceptable carrier is hydrophilic and has a molecular weight of less than 1,000 Daltons, and is selected from one or more of the group consisting of tartaric acid, a sugar, and a sugar alcohol; and
   the amount of the pharmaceutically acceptable carrier to therapeutic agent in the therapeutic layer is from 1:8 to 4:1 wt/wt.

2. The medical device according to claim 1, wherein the medical device is a catheter balloon for a balloon catheter or is a balloon catheter.

3. The medical device according to claim 1, wherein:
   (a) the hydrophilic polymer and/or a hydrophilic compound in the adhesion balance layer contains hydrogen bonding moieties; and/or
   (b) the drug particles have at least one dimension that is less than 15 μm; and/or
   (c) one or more of the group selected from particulate needles, microparticles and nanoparticles.

4. The medical device according to claim 1, wherein the adhesion balance layer swells or absorbs water when in contact with water.

5. The medical device according to claim 1, wherein the adhesion balance layer further comprises a hydrophobic polymer.

6. The medical device according to claim 5, wherein the polymer layer contains less than 30 wt % of the hydrophobic polymer and/or wherein the hydrophilic polymer and/or hydrophobic polymer is not shellac.

7. The medical device according to claim 1, wherein the hydrophilic polymer is a block copolymer comprising hydrophobic and hydrophilic blocks.

8. The medical device according to claim 1, wherein the therapeutic agent of the therapeutic agent layer is selected from one or more of the group consisting of an antiproliferative, immunosuppressive, anti-angiogenic, anti-inflammatory, and anti-thrombotic agent.

9. The medical device according to claim 1, wherein the adhesion balance layer further comprises a therapeutic agent.

10. The medical device according to claim 1, wherein the pharmaceutically acceptable carrier is selected from one or more of the group consisting of xylitol and tartaric acid.

11. The medical device according to claim 1, wherein the balloon forms an integral or removable part of a balloon catheter.

12. A process to make a drug-coated medical device according to claim 1 wherein the process comprises:
    (a) providing an uncoated balloon;
    (b) providing an adhesion balance layer precursor mixture, coating at least part of the outer surface of balloon with the adhesion balance layer precursor mixture to form an adhesion balance layer precursor layer and drying the adhesion balance layer precursor layer to provide a balloon coated with an adhesion balance layer;
    (c) providing a therapeutic agent mixture and coating the therapeutic agent solution onto the outer surface of the balloon coated with an adhesion balance layer, followed by drying the coated balloon to provide the drug-coated catheter balloon, wherein
    therapeutic agent mixture comprises a hydrophobic therapeutic agent with one or more hydrogen-bonding groups, a solvent and a hydrophilic pharmaceutically acceptable carrier that has a molecular weight of less than 1,000 Daltons, wherein the pharmaceutically acceptable carrier is selected from one or more of the group consisting of tartaric acid, a sugar, and a sugar alcohol, and wherein the amount of hydrophilic pharmaceutically acceptable carrier to hydrophobic therapeutic agent in the therapeutic agent mixture is from 1:8 to 4:1 wt/wt; and
    the adhesion balance layer precursor mixture comprises a hydrophilic polymer and/or a hydrophilic compound, where the hydrophilic polymer has a number average molecular weight of from 10,000 to 10,000,000 Daltons and the hydrophilic compound has a molecular weight of less than 1,000 Daltons.

13. The process according to claim 12, wherein the process further comprises the steps of:
    (i) inflating the balloon between step (a) and (b);
    (ii) deflating the balloon following step (c); and
    (iii) folding the balloon following step (ii).

14. The process according to claim 13, wherein the adhesion balance layer precursor mixture further comprises a hydrophobic polymer.

15. The process according to claim 12, wherein:
    (a) the medical device is a balloon catheter and the balloon is integrally formed as part of the balloon catheter; or
    (b) the process further comprises fixing the balloon onto a balloon catheter either as a removable or integral part of said balloon catheter to form the medical device.

16. A method of treatment comprising administering an effective amount of a drug to a tissue in need of said treatment, wherein said administering involves contacting said tissue with a drug-coated medical device according to claim 1.

17. The method of treatment of claim 16, wherein the method further comprises the steps of:

(a) inserting the drug-coated medical device into a hollow tissue of a subject;
(b) advancing the medical device to a target site in a tissue;
(c) inflating the balloon and maintaining the inflated state for a period of time sufficient for the therapeutic agent to adhere to the target site;
(d) deflating the balloon and removing the medical device from the subject.

18. The drug-coated medical device according to claim 1, wherein:
the therapeutic layer comprises crystals of the therapeutic agent, and the device is configured to release a sustainable therapeutically effective amount of the therapeutic agent from the therapeutic layer within a time period of 1 second to 2 minutes after reaching a desired site of action.

* * * * *